United States Patent
Coats

[19]

[11] Patent Number: 6,074,207
[45] Date of Patent: Jun. 13, 2000

[54] ORTHODONTIC DEVICE FOR REPOSITIONING THE MOLARS

[76] Inventor: Matthew J. Coats, 6204 Parade Field Way, Lansdale, Pa. 19446

[21] Appl. No.: 09/055,499

[22] Filed: Apr. 6, 1998

[51] Int. Cl.⁷ .................................................. A61C 3/00
[52] U.S. Cl. .................................. 433/19; 433/6; 433/18
[58] Field of Search ............................ 433/19, 6, 17, 433/18

[56] References Cited

U.S. PATENT DOCUMENTS

| | | | |
|---|---|---|---|
| 4,424,032 | 1/1984 | Howe | 433/19 |
| 4,462,800 | 7/1984 | Jones | 433/19 |
| 4,795,342 | 1/1989 | Jones | 433/19 |
| 4,969,822 | 11/1990 | Summer | 433/19 |
| 5,022,855 | 6/1991 | Jeckel | 433/6 |
| 5,067,896 | 11/1991 | Korn | 433/6 |
| 5,299,935 | 4/1994 | Lokar | 433/18 |
| 5,352,116 | 10/1994 | West | 433/19 |
| 5,499,633 | 3/1996 | Fenton | 433/6 |
| 5,645,423 | 7/1997 | Collins, Jr. | 433/21 |
| 5,645,424 | 7/1997 | Collins | 433/21 |
| 5,678,990 | 10/1997 | Rosenberg | 433/19 |
| 5,697,781 | 12/1997 | Ellingson | 433/19 |

*Primary Examiner*—John J. Wilson
*Attorney, Agent, or Firm*—LaMorte & Associates

[57] ABSTRACT

An orthodontic device and associated method for altering the position of a tooth in the mouth. The orthodontic device includes a bracket that attaches to the tooth or teeth that are to be moved. A bite plate is produced that is contoured to engage teeth on both the maxillary arch and the mandibular arch, other than the tooth to be moved. The bite plate can be a single piece unit or a two piece unit that can be joined within the mouth. A spring element is disposed between the bite plate and the bracket. The spring element applies a spring bias between the bracket and the bite plate. Since the spring bias acts on the tooth to be moved and the bite plate, the spring bias acts to correct the position of the tooth to be moved without any significant effect on the other teeth in the mouth.

15 Claims, 3 Drawing Sheets

ORTHODONTIC DEVICE FOR REPOSITIONING THE MOLARS

BACKGROUND OF THE INVENTION

1. Field of the Invention

The present invention relates to orthodontic methods and devices that are used to change the position of a tooth within the mouth. More specifically, the present invention relates to orthodontic methods and devices that are used to move individual molars either backward or forward in the mouth.

2. Description of Related Art

Not every person is born with perfectly straight teeth and a perfect bite. As is well known, very few people are born with the blessing of perfect teeth. Those without perfect teeth must therefore either live out their lives with imperfect teeth or have the position of the teeth somehow artificially altered. The science of artificially altering the position of a person's teeth is most commonly studied in the field of orthodontics, wherein the various devices used to alter the position of the teeth are referred to as orthodontic devices.

One of the most common orthodontic devices used to alter the position of teeth involves the use of "braces" wherein brackets are attached to individual teeth and the brackets are interconnected by an arch wire. By periodically tightening the tension of the arch wire, a corrective force can be applied to misaligned teeth. Over time, the corrective force causes the teeth to change in position, thereby correcting the problem of misalignment.

A problem commonly encountered in the field of orthodontics is the problem of how to counter the corrective force being applied to a tooth by an orthodontic device. For example, if an orthodontic device was positioned between an aligned tooth and a misaligned tooth, the forces applied by the orthodontic device would be just as likely to move the aligned tooth as it would be to correct the misaligned tooth. The way this problem is typically corrected is to attach orthodontic devices between a few misaligned teeth and a multitude of properly aligned teeth. In this manner, it is much more likely that the few misaligned teeth will be influenced by the forces created by the orthodontic device, rather than the multitude of properly aligned teeth.

However, there is one instance where this general orthodontic anchoring principal does not work. In many instances, a person's molars may be positioned at an abnormally forward position in either the maxillary arch or the mandibular arch. The forward position of the molars do not leave room in the bite line for the premolars, canine teeth and incisors. Consequently, either some or all of the premolar, canine and incisor teeth may grow to be misaligned. Prior to correcting the position of a misaligned incisor, canine tooth or premolar, room must be made in the bite line for that tooth. To make the necessary room, the molars must either be removed or moved back to a point deeper in the mouth.

The molars are the largest of the teeth with the strongest root system. Accordingly, the molars are harder to move than are most other teeth. As a result, if a molar is biased against other teeth with an orthodontic device, there is a good chance that the other teeth may be adversely effected. Furthermore, since the molars are the rear most teeth in the mouth, there is nothing deeper in the mouth to which an orthodontic device can be anchored in order to move the molar further into the mouth. In the prior art, this problem is typically solved using a head harness system. In such a prior art system, a harness is placed around the head. An orthodontic device is attached to the molars and then to the harness. The entire head therefore acts as an anchoring point for the orthodontic device.

Head harnesses are very cumbersome and uncomfortable. Furthermore, they are not aesthetically pleasing. For these reasons, people typically only wear such harnesses at night in the privacy of their own homes.

A need therefore exists in the art for an orthodontic system that can be used to move the molars, wherein the anchor point for that orthodontic system is contained completely within the mouth. This need is met by the present invention device and method as described and claimed below.

SUMMARY OF THE INVENTION

The present invention is an orthodontic device and associated method for altering the position of a tooth in the mouth. The orthodontic device includes a bracket that attaches to the tooth or teeth that are to be moved. A bite plate is produced that is contoured to engage teeth on both the maxillary arch and the mandibular arch, other than the tooth to be moved. The bite plate can be a single piece unit or a two piece unit that can be joined within the mouth. A spring element is disposed between the bite plate and the bracket. The spring element applies a spring bias between the bracket and the bite plate. Since the spring bias acts on the tooth to be moved and the bite plate, the spring bias acts to correct the position of the tooth to be moved without any significant effect on the other teeth in the mouth.

BRIEF DESCRIPTION OF THE DRAWINGS

For a better understanding of the present invention, reference is made to the following description of two exemplary embodiments thereof, considered in conjunction with the accompanying drawings, in which.

DETAILED DESCRIPTION OF AN EXEMPLARY EMBODIMENT

Although the present invention apparatus and method can be used to move most any tooth in a person's mouth, the present invention is particularly well suited for moving either the first, second or third set of molars. Accordingly, by way of example, the present invention apparatus and method will be described in an application where a set of molars must be moved either rearward or forward in the mouth.

Figure 1:
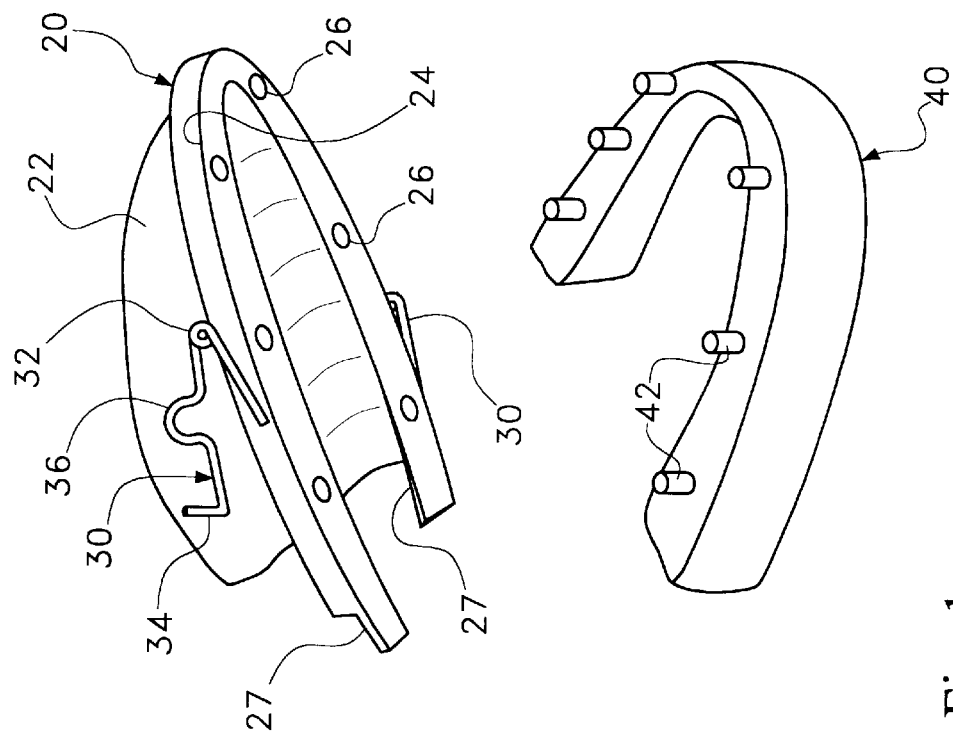
FIG. 1 is perspective view of one embodiment of an orthodontic device used in accordance with the present invention. The orthodontic device is shown in conjunction with a mouth that has the lips selectively cut away to clearly illustrate the teeth.
Figure 1:
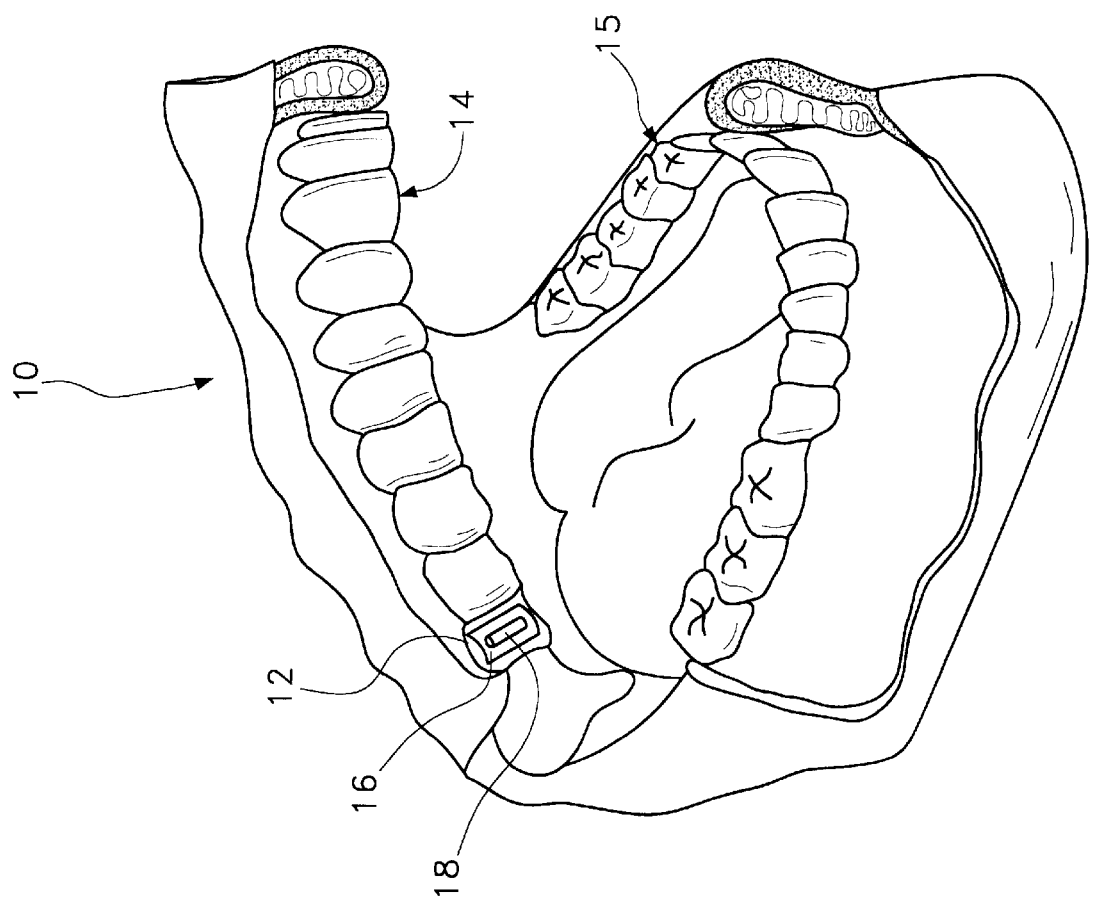

Referring to FIG. 1, a patient's mouth 10 is shown. By way of example, it is to be assumed that the patient requires that the set of second molars 12 in the maxillary arch 14 must be moved rearwardly before orthodontic procedures can be used to correct other teeth.

A bracket 16 is bonded to each of the second molars 12 using traditional bracket anchoring techniques. Each bracket 16 contains a receptacle 18 for receiving a spring post. The receptacle 18 is a cylindrical tube having an open top surface and an open bottom surface. The receptacle 18 is affixed to the bracket 16 in a vertical orientation. As such, the receptacle 18 is oriented with the length of the tooth to which it is affixed. Each bracket 16 is affixed to the tooth or teeth that are to be moved. In the exemplary embodiment shown, no third molar is present and it is the second molar 12 that is to be moved. It should be understood that if a set of third molars were present and both the third and second molars were to be moved, brackets would attach to both second molars and the third molars.

A maxillary bite plate 20 is provided. A custom maxillary bite plate 20 is created for each patient using traditional impression modeling techniques. The maxillary bite plate 20 has a central region 22 that is shaped to conform to the hard palate of the patient. A bite surface 24 extends from the forward edges of the central region 22. The bite surface 24 contains impressions of at least some of the teeth in the maxillary arch 14 that lay forward of the set of second molars 12. An optional lip region 27 may extend rearwardly from the bite surface 24. The lip region 27 passes over the tooth to be moved without physically engaging that tooth. Blind bores 26 are disposed along the bottom exterior of the maxillary bite plate 20. The purpose of the lip region 27 and the bores 26 will later be explained.

Two spring elements 30 are anchored into the material of the maxillary bite plate 20, wherein each spring element 30 is the mirror image of the other. Each spring element 30 extends forward, out of the material of the maxillary bite plate 20. A coil configuration 32 is formed in each spring element 30 that reverses the direction of the spring element 30, thereby causing the spring element 30 to lead back toward the rear of the maxillary bite plate 20. The free end of the spring element 30 is formed into a post 34. The post 34 is sized to engage the post receptacle 18 that is formed on the bracket 16 bonded to each second molar 12. The segment of spring element 30 between the post 34 and the coil configuration 32 contains an arch configuration 36. The purpose of the coil configuration 32 and the arch configuration 34 in the spring element 30 will be later explained.

A mandibular bite plate 40 is also provided. The mandibular bite plate 40 contains impressions of at least some of the teeth contained in the mandibular arch 15. The mandibular bite plate 40 is made for each patient by taking an impression of the patent's teeth using traditional modeling techniques. Joining posts 42 extend upwardly from the to surface of the mandibular bite plate 40. The joining posts 42 are positioned and sized to engage the bores 26 on the bottom of the maxillary bite plate 20, for a reason that will later be explained.

Figure 2:
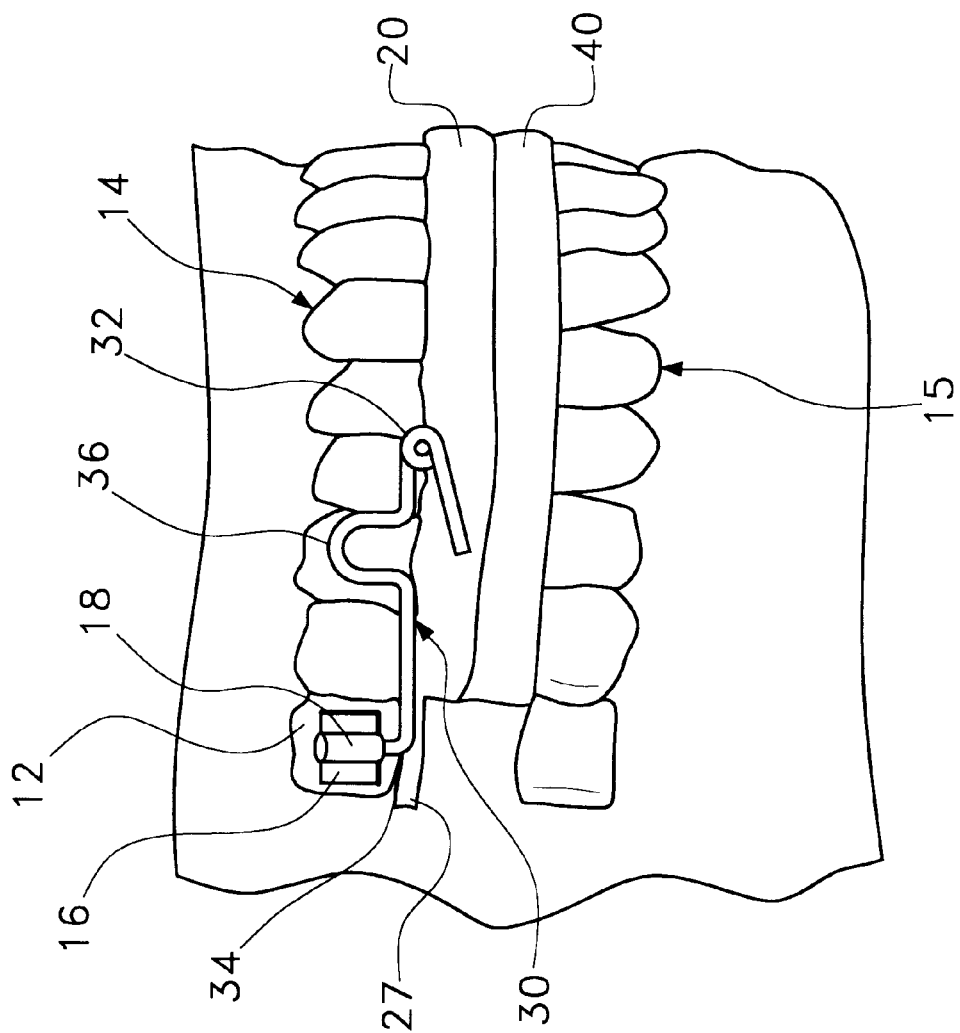
FIG. 2 is a side view of the exemplary embodiment of FIG. 1.

Referring to FIG. 2, it can be seen that when the maxillary bite plate 20 is placed into the mouth, the maxillary bite plate 20 engages all of the teeth in the maxillary arch 14 that lay forward to the molars 12 to be moved. The maxillary bite plate 20 also engages the hard palate within the mouth. As such, the maxillary bite plate 20 engages the hard palate, the first molars, the premolars, the canine teeth and the incisors, thereby creating a strong intermouth anchor against which an orthodontic device can be biased.

The spring elements 30 are positioned relative the maxillary bite plate 20 so that the post 34 of the spring element 30 lays near the bracket 16 on the molar 12 to be moved. The post 34 of the spring element 30 is placed within the post receptacle 18 on the bracket 16. The coil configuration 32 on the spring element 30, biases the post 34 into the receptacle 18 so it does not fall out of position. The arch configuration 36 in the spring element 30 becomes slightly deformed as the post 34 of the spring element 30 is placed within the receptacle 18 of the bracket 16. The deformation of the arch configuration 36 causes a spring bias that can act to either push the bracket 16 away from the maxillary bite plate 20 or pull the bracket 16 closer to the maxillary bite plate 20. In the example cited, it is desired to move the second molar 12 further back into the mouth. As such, the arch configuration 36 is formed to bias the bracket 16 on the second molar 12 away from the maxillary bite plate 20. The bias of the spring element 30 acts against the second molar 12, via the bracket 16. That same spring bias also acts against the maxillary bite plate 20 which is anchored to all the remaining teeth in the maxillary arch 14 as well as the hard palate. Consequently, tooth movement caused by the spring element 30 is experienced essentially solely by the second molar 12.

To reinforce the anchoring of the spring element 30, the maxillary bite plate 20 engages the mandibular bite plate 40 within the patient's mouth. The mandibular bite plate 40 conforms to all of the teeth present on the mandibular arch 15. When set in place, the joining posts 42 (FIG. 1) that extend upwardly from the mandibular bite plate 40 engage the blind bores 26 (FIG. 1) in the bottom of the maxillary bite plate 20. The positioning of the joining posts in the bores acts to mechanically interconnect the maxillary bite plate 20 and the mandibular bite plate 40. Accordingly, the maxillary bite plate 20 cannot move without the mandibular bite plate 40. The anchored end of the spring element 30 is therefore supported by all of the teeth on the mandibular arch 15, all of the teeth on the maxillary arch 14 that lay in front of the second molar 12, and the hard palate. The spring element 30 therefore provides a spring bias that acts between the molars 12 to be moved and essentially every other tooth in the mouth. Such a distribution of force ensures that only the desired molars 12 move without effect to the other teeth.

In FIG. 2, it can be seen that the lip region 27 the extends from the maxillary bite plate 20 lays under the tooth being moved. The lip region prevents the spring elements 30 from moving the tooth in a downwardly direction and accidentally extruding the tooth. Consequently, all movement of the tooth is directed in the desired direction of movement.

Figure 3:
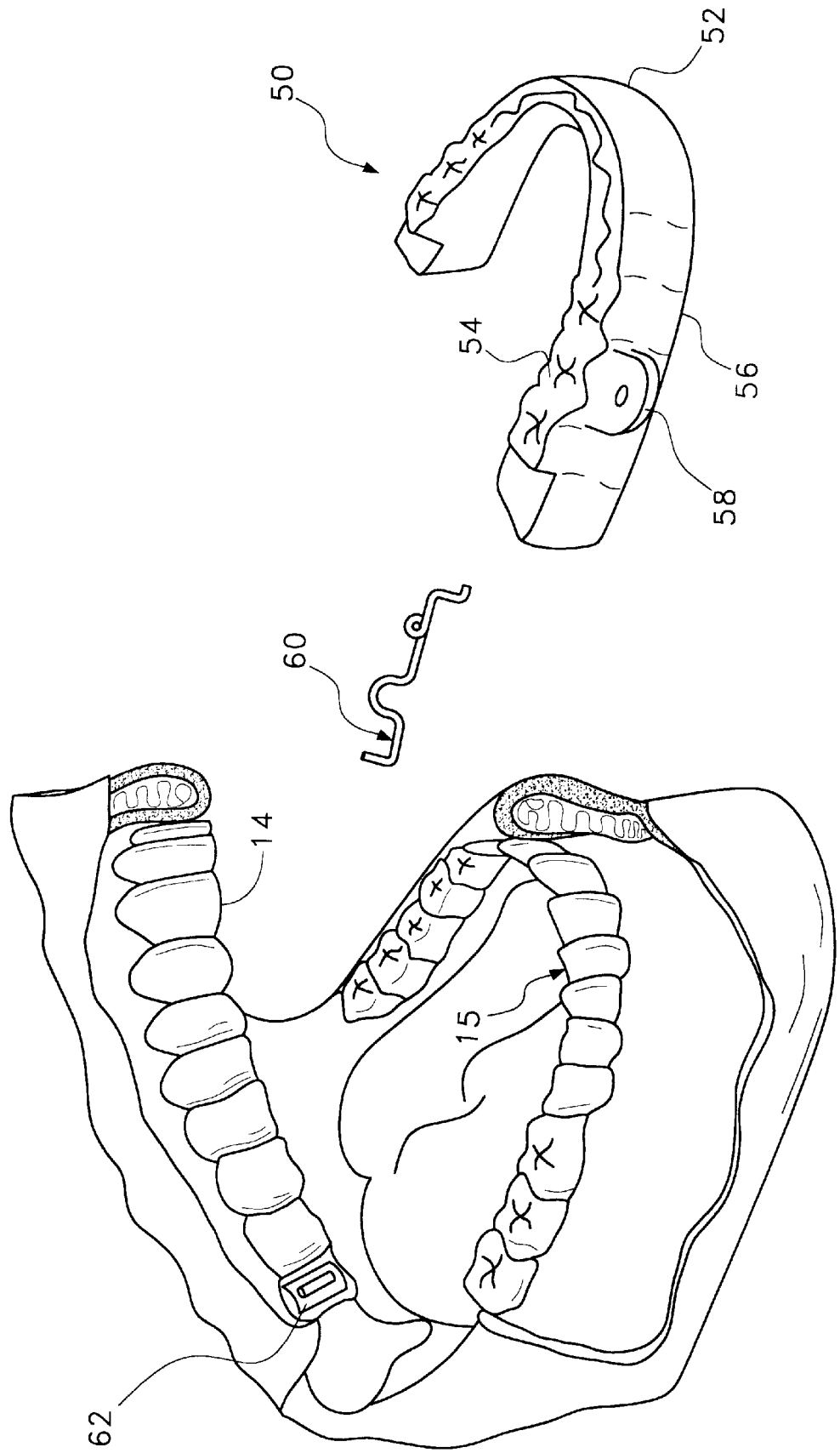
FIG. 3 shows a perspective view of an alternate embodiment of an orthodontic bracket in accordance with the present invention.

Referring to FIG. 3, an alternate embodiment of the present invention orthodontic device 50 is shown. In this embodiment, only a single bite plate 52 is provided. The bite plate 52 has an upper surface 54 that conforms to the teeth in the maxillary arch 14 that are not being moved and a lower surface 56 that conforms to the teeth in the mandibular arch 15. When a person bites onto the bite plate 52, the bite plate 52 engages all of the teeth in the mouth except the teeth that are to be moved.

In this embodiment, a small protrusion 58 extends outwardly from each side of the bite plate 52. The protrusions 58 are adapted to receive one end of a spring element 60. The spring element 60 engages a bracket 62 that is bonded to the tooth that is to be moved in the manner previously described. The spring element 60 applies a spring bias that acts between the tooth to be moved and the bite plate 52. Since the bite plate 52 is anchored to all of the remaining teeth in the mouth, the spring bias provided by the spring element 30 effects only the tooth to be moved.

In the embodiments described, the spring element is being used to move a molar further back into the mouth. It should be understood that the same configuration can be used to move a molar further forward in the mouth. This is accomplished by configuring the spring element so it pulls on the molar rather than pushes the molar when the orthodontic device is in use.

The method of producing the present invention orthodontic device includes the steps of making impressions of the teeth in the maxillary arch and the mandibular arch that are not to be moved. From these impressions a bite plate is to be formed using traditional modeling techniques. The bite plate can be a single bite plate, such as was shown in FIG. 3 or can be a two piece interlocking bite plate as was shown in FIG. 1.

The spring element is then formed. The shape of the spring element will vary depending upon the location of the tooth to be moved and the dimensions of the mouth. The spring element is shaped to apply the proper corrective force in the proper direction to the tooth to be moved.

A bracket is coupled to the tooth to be moved using conventional bonding techniques. The spring element is then attached to both the bite plate and the bracket so that the spring element applies the required spring bias between the bite plate and the bracket. The spring element may be permanently anchored to the bite plate or removeably attachable to the bite plate as a matter of design choice.

It will be understood that the specifics of the apparatus and method described are merely exemplary and that the present invention can be practiced using functionally equivalent components and/or method steps. For example, different spring element configurations can be used in place of the configuration shown. Furthermore, the position of the spring elements can be changed to the lower bite plate if molars on the mandibular arch are to be moved. All such modifications and alternate embodiments are intended to be included within the scope of the present invention as defined by the below appended claims.

What is claimed is:

1. An orthodontic device for altering the position of a tooth in the mouth, said device comprising:

a bracket that is attachable to the tooth to be moved;

a bite plate being contoured to engage at least a majority of teeth in the mouth, other than the tooth to be moved, when bit upon, said bite plate including a first segment that engages at least some teeth of the maxillary arch and a separate second segment that engages at least some the teeth of the mandibular arch;

an engagement mechanism for interconnecting said first segment and said second segment of said bite plate when in the mouth; and a spring element disposed between said bite plate and said bracket for applying a spring bias between said bracket and said bite plate.

2. The device according to claim 1, wherein said spring element is anchored at one end to said bite plate.

3. The device according to claim 1, wherein said bite plate contains at least one protrusion extending therefrom that is adapted to selectively receive at one end of said spring element.

4. The device according to claim 1, wherein said spring bias supplied by said spring element biases said bracket away from said bite plate.

5. The device according to claim 1, wherein said spring bias supplied by said spring element biases said bracket toward said bite plate.

6. The device according to claim 1, wherein said first segment of said bite plate further includes a segment that engages the hard palate within the mouth.

7. The device according to claim 1, wherein said spring element has a first end that engages said bracket, a second end that engages said bite plate and an arch configuration disposed between said first end and said second end for providing said spring bias.

8. A method of altering the position of a tooth, comprising the steps of:

affixing a bracket to the tooth to be moved;

providing a removable bite plate that engages a majority of teeth in the mouth other than the tooth to be moved, said bite plate including a first plate that engages at least some teeth of the maxillary arch and a second plate that engaged at least some teeth of the mandibular arch;

providing an engagement mechanism for joining said first plate to said second plate within the mouth; and positioning a spring element between said bracket and said bite plate, wherein said spring element supplies a spring bias that acts between said bracket and said bite plate.

9. The method according to claim 8, wherein the step of providing a bite plate includes the substeps of:

taking a first impression of teeth in the maxillary arch;

taking a second impression of teeth in the mandibular arch; and forming said first plate and said second plate from said first impression and said second impression, respectively.

10. The method according to claim 8, wherein the step of providing a bite plate includes the substeps of:

taking a first impression of teeth in the maxillary arch;

taking a second impression of teeth in the mandibular arch;

making said first plate from said first impression; and making said second plate from said second impression.

11. The method according to claim 8, wherein said step of positioning a spring element between said bracket and said bite plate includes anchoring one end of said spring element into the material of said bite plate.

12. An orthodontic device for moving a tooth within the mouth, comprising:

a maxillary bite plate for engaging at least some teeth in the maxillary arch;

a mandibular bite plate for engaging at least some teeth in the mandibular arch;

a mechanism of selectively interconnecting said maxillary bite plate to said mandibular bite plate within the mouth;

a spring element having a first end and a second end, wherein said second end of said spring element is affixed to said maxillary bite plate; and a bracket adapted to be affixed to the tooth to be moved, wherein said bracket contains a receptacle for receiving said first end of said spring element.

13. The device according to claim 12, wherein said spring element supplies a spring bias that biases said bracket away from said maxillary bite plate.

14. The device according to claim 12, wherein said spring element supplies a spring bias that biases said bracket toward said maxillary bite plate.

15. The device according to claim 12, wherein said maxillary bite plate further includes a segment that engages the hard palate within the mouth.

* * * * *